United States Patent [19]
Kitajima et al.

[11] Patent Number: 6,057,308
[45] Date of Patent: May 2, 2000

[54] REMEDY OR PREVENTIVE FOR HYPERLIPEMIA

[75] Inventors: Hideaki Kitajima; Kenji Tsunoda, both of Tokyo; Teruyoshi Yanagita, Saga; Shigeru Murakami, Tokyo, all of Japan

[73] Assignee: Taisho Pharmaceutical Co., Ltd., Japan

[21] Appl. No.: 09/180,745

[22] PCT Filed: May 29, 1996

[86] PCT No.: PCT/JP96/01443

§ 371 Date: Nov. 17, 1998

§ 102(e) Date: Nov. 17, 1998

[87] PCT Pub. No.: WO97/45112

PCT Pub. Date: Dec. 4, 1997

[51] Int. Cl.$^7$ ............................ A61K 31/56; A61K 31/13
[52] U.S. Cl. ............................................. 514/171; 514/665

[58] Field of Search ...................................... 514/171, 665

[56] References Cited

PUBLICATIONS

CA 120:297323, Venkatesan et al., 1993.
CA 118:622, Ito et al., 1992.

*Primary Examiner*—Kimberly Jordan
*Attorney, Agent, or Firm*—Lorusso & Loud

[57] ABSTRACT

[Object] : To provide a pharmaceutical preparation for treating or preventing hyperlipemia which lowers cholesterols and neutral fats in blood and has a property to improve lipoprotein metabolism.

[Construction] : A pharmaceutical preparation for treating or preventing hyperlipemia comprising taurine and γ-oryzanol as effective components.

4 Claims, No Drawings

REMEDY OR PREVENTIVE FOR HYPERLIPEMIA

This application is a 371 of PCT/JP96/01443, filed May 29, 1996.

TECHNICAL FIELD

The present invention relates to a pharmaceutical reparation for treating or preventing hyperlipemia.

BACKGROUND ART

Blood lipid components such as cholesterols, neutral fats, phospholipids or free fatty acids are in the form of water-soluble lipoproteins in the blood, which are classified into very-low-density lipoprotein (VLDL), low-density lipoprotein (LDL) and high-density lipoprotein (HDL) by the difference of density. Hyperlipemia is in a status of higher blood concentration of these lipid components which is caused by abnormal lipoprotein metabolism in the body than the normal concentration. When the status of hyperlipemia is continued for a long term, cholesterol and the like tend to deposit into the artery wall, and it has been found by many investigations and epidemiological research that atherosclerosis such as myocardial infarction, angina pectoris or cerebral infarction originates and develops. Accordingly, it is important to lower the blood concentration of these lipid components to the normal concentration for treating hyperlipemia, and it is important to maintain the normal concentration for preventing hyperlipemia.

Taurine (aminoethylsulfonic acid) is a sulfur-containing amino acid having a very simple chemical structure with a molecular weight of 125.14, and known to have various pharmacological properties, over a broad area beginning with central nervous system, circulatory system and hepatobiliary system. Concerning the properties of taurine to the cholesterol metabolism, there are also known the lowering effect of serum cholesterol via cholagogic function and inhibition of gallstone formation by cholesterol.

γ-Oryzanol is known to have the properties to inhibit the absorption of cholesterol and improve the lipoprotein metabolism.

For treating hyperlipemia at the present time, dietetic therapy is first applied, and when it is not sufficiently effective, drug theraphy needs to be applied.

Recently, there are some pharmaceutical drugs of hyperlipemia with different mechanism of action (absorption inhibition, excretion acceleration and synthesis inhibition), but they have a problem of the side-effects, main examples of which are leukocyte decrease, hepatic enlargement, gastrointestinal troubles, sexuality reduction, etc. Accordingly, a pharmaceutical drug for treating or preventing hyperlipemia without side-effects is desirable.

In view of preventive medicine, a desired drug for preventing the origination of hyperlipemia is one which maintains the low blood concentration of lipid components (e.g. cholesterols, neutral fats, phospholipids and free fatty acids), has no side-effect, and can be administered safely for a long term.

An object of the present invention is to provide a pharmaceutical preparation of treating or preventing hyperlipemia which is safe even if applied for a long term.

DISCLOSURE OF THE INVENTION

The present inventors have found that an administration of taurine and γ-oryzanol at the same time has a greater effect to improve the metabolism of excess amount of lipid components in the body such as cholesterol than an administration of either taurine or γ-oryzanol alone, and have accomplished the present invention by the finding.

Accordingly, the present invention relates to a pharmaceutical preparation for treating or preventing hyperlipemia comprising taurine and γ-oryzanol as effective components.

The pharmaceutical preparation for treating or preventing hyperlipemia of the present invention lowers the blood concentration of excess amount of lipid components in the body (e.g. cholesterols, neutral fats, phospholipids and free fatty acids), and has a property to improve lipoprotein metabolism, thereby it is useful as a pharmaceutical preparation for treating or preventing hyperlipemia, especially, it is very useful as a pharmaceutial preparation for preventing hyperlipemia because it has no side-effect and can be administered safely for a long term.

According to the present invention, the effective dose of taurine is from 100 mg to 6000 mg for a healthy adult per day, preferably 1000 mg to 3000 mg. The effective dose of γ-oryzanol is from 1 mg to 6000 mg for a healthy adult per day, preferably 5 mg to 500 mg. The amount ratio of taurine to γ-oryzanol is 300 : 1~30.

The pharmaceutical preparation for treating or preventing hyperlipemia of the present invention can 15 contain other known additives, if desired, for example, fillers, disintegrators, binders, lubricants, anti-oxidants, coating agents, coloring agents, corrigents, surfactants, plasticizers and like, and can be formulated in the form of granules, powders, capsules, tablets, dry-syrups or solutions according to an ordinary method.

The pharmaceutical preparation of the present invention containing taurine and γ-oryzanol as effective components is more effective to treat or prevent hyperlipemia by further addition of pantethine and nicotinic acid thereto.

Furthermore, if desired, one or more vitamins, other physiologically effective components, hormones, nutrient components, perfumes and the like can be added.

INDUSTRIAL APPLICABILITY

The pharmaceutical preparation of the present invention containing taurine and γ-oryzanol as effective components lowers the blood concentration of cholesterols and neutral fats, and has a property to improve lipoprotein metabolism, therefore, it is useful as a pharmaceutical preparation for treating or preventing hyperlipemia, and especially, it is very useful as a pharmaceutical preparation for preventing hyperlipemia because it has no side-effect and can be administered safely for a long term.

BEST MODE FOR CARRYING OUT THE INVENTION

The present invention is illustrated in more detail by the following examples and experiments.

EXAMPLE 1

| | |
|---|---|
| Taurine | 3000 mg |
| γ-Oryzanol | 10 mg |
| Powder sugar | 600 mg |
| Aerosil | 36 mg |
| Aspartame | 9 mg |
| Low substituted hydroxypropyl cellulose | 54 mg |

Following an ordinary method, there were obtained granules containing the above-mentioned components.

EXAMPLE 2

| | |
|---|---|
| Taurine | 3000 mg |
| γ-Oryzanol | 10 mg |
| Vitamin E | 100 mg |
| Powder sugar | 600 mg |
| Aerosil | 600 mg |
| Aspartame | 9 mg |
| Low substituted hydroxypropyl cellulose | 54 mg |
| Magnesium stearate | 24 mg |
| Pigment | trace |
| Perfume | trace |

Following an ordinary method, there were obtained granules containing the above-mentioned components.

EXAMPLE 3

| | |
|---|---|
| Taurine | 3000 mg |
| Pantethine | 50 mg |
| γ-Oryzanol | 10 mg |
| Powder sugar | 600 mg |
| Aerosil | 36 mg |
| Aspartame | 9 mg |
| Low substituted hydroxypropyl cellulose | 54 mg |

Following an ordinary method, there were obtained granules containing the above-mentioned components.

EXAMPLE 4

| | |
|---|---|
| Taurine | 3000 mg |
| γ-Oryzanol | 10 mg |
| Vitamin E | 100 mg |
| Vitamin $B_1$ | 10 mg |
| Vitamin $B_2$ | 20 mg |
| Vitamin $B_6$ | 10 mg |
| Vitamin C | 600 mg |
| Nicotinic acid | 10 mg |
| Pantethine | 50 mg |
| Starch | 600 mg |
| Low substituted hydroxypropyl cellulose | 12 mg |
| Aspartame | 12 mg |
| Magnesium stearate | 24 mg |

Following an ordinary method, there were obtained granules containing the above-mentioned components.

Experiment 1: Effect on SHRSP (spontaneously hypertensive rats stroke-prone) by fat-enriched diet

[Experimental Animals]

Six male SHRSP, 3 months of age, were used for each group.

[Experimental Group]

Each group of rats was treated with the granules obtained in Example 1 per day (Example 1 treated group), 3000 mg of taurine (Taurine treated group), 300 mg of γ-Oryzanol (γ-Oryzanol treated group) and not treated with any drug (Fat-enriched diet group).

[Diet]

Each group was fed fat-enriched diet. The fat-enriched diet refers to a diet which is obtained by adding 5% cholesterol, 2% cholic acid and 20% beef tallow to a basal diet. The basal diet is obtained from the following composition wherein the vitamin mixture and mineral mixture were the same as described by Harper (J. Nutr., 67, 109 (1959)).

Composition of Basal Diet

| | |
|---|---|
| Casein | 18.0% |
| Fat | 5.0% |
| Vitamin mixture | 1.0% |
| Mineral mixture | 4.0% |
| Choline chloride | 0.2% |
| Cellulose | 9.6% |
| Sucrose | 62.2% |
| Total | 100.0% |

[Experimental Method]

Each group of rats was fed the diet and was bred for 45 days. After the feeding, the blood was collected via the caudal vein of animals to measure the serum cholesterol concentration. After the end of breeding, the liver was excised to measure the cholesterol concentration.

In addition, the mesenteric artery was excised, the surrounding fat was stripped and dyed with Sudan III, and number of fat depositions was counted by microscopy to determine the inhibition rate of fat deposition of the mesenteric artery.

[Results]

The serum cholesterol concentrations are shown in Table 1. The serum cholesterol concentration in Example 1 treated group was kept lower than that in the other groups. The inhibition rate of the liver cholesterol is calculated from the liver cholesterol concentration according to the following formula:

$$\frac{\text{Inhibition rate}}{\text{of cholesterol}} = \frac{\text{Control group score} - \text{Each group score}}{\text{Control group score}} \times 100$$

The liver cholesterol concentration and the inhibition rate of liver cholesterol are shown in Table 2. The liver cholesterol concentration in Example 1 treated group was kept low and the inhibition rate of the fat deposition in Example 1 treated group was high, in comparison with the other groups.

In addition, the deposition of fat was judged by four stages of the number of depositions as 0 to 20, 20 to 100, 100 to 200 and more than 200, which were scored to 1, 2, 3 and 4, respectively, an average score of each group was calculated, and the inhibition rate of the fat deposition of the mesenteric artery in each group is calcurated according to the following formula.

$$\frac{\text{Inhibition rate}}{\text{of fat deposition}} = \frac{\text{Control group score} - \text{Each group score}}{\text{Control group score}} \times 100$$

Table 3 shows average scores of the fat deposition in each group and the inhibition rate of the fat deposition in the mesenteric artery. The inhibition rate of the fat deposition in Example 1 treated group was high in comparison with the other groups.

TABLE 1

| Experimental Group | Immediately after | After 25 days | After 45 days |
|---|---|---|---|
| Example 1 treated group | 54.6 | 115.8 | 188.1 |

TABLE 1-continued

| Experimental Group | Immediately after | After 25 days | After 45 days |
|---|---|---|---|
| Taurine treated group | 55.2 | 225.5 | 365.6 |
| γ-Oryzanol treated group | 53.7 | 399.4 | 553.2 |
| Fat-enriched diet group | 57.8 | 427.7 | 767.5 |

TABLE 2

| Experimental Group | Cholesterol concentration (mg/g tissue) | Inhibition rate (%) |
|---|---|---|
| Example 1 treated group | 26.67 | 55.9 |
| Taurine treated group | 53.33 | 11.9 |
| γ-Oryzanol treated group | 44.92 | 25.8 |
| Fat-enriched diet group | 60.51 | — |

TABLE 3

| Experimental Group | Score | Inhibition rate (%) |
|---|---|---|
| Example 1 treated group | 0.78 | 70.8 |
| Taurine treated group | 1.20 | 55.1 |
| γ-Oryzanol treated group | 2.21 | 17.2 |
| Fat-enriched diet group | 2.67 | — |

Experiment 2: Effect of secretion of fat on Hep G2 cell

[Experimental Group]

T+γ Group is treated with 2.0 mM taurine and 0.05 mM γ-Oryzanol, T group is treated with 2.0 mM taurine only, and C group is untreated with any drug as a control group.

[Experimental Method]

Experiment 2 is carried out by the method described in Current Therapeutic Research, vol. 58, No. 8, 787–795 (1995).

1. Preparation of Experimental Medium and Addition Method of Drug

Dulbecco's Modified Eagle's medium (DMEM) (glucose concentration, 4500 mg/ml) containing 10% lipoprotein deficient serum (LPDS) was used as a basal medium. Taurine was dissolved in phosphate-buffered saline (PBS), sterilized by filtration and added to the basal medium to be made up to the concentration of 2.0 mM to give a test medium. γ-Oryzanol was dissolved in dimethyl sulfoxide (DMSO) to be made up to the concentration of 0.05 mM, and added to the basal medium. Cells cultured in the medium containing PBS (concentration of 1%) were used as a control.

2. Culture of Cells and Recovery of Cells and Medium

Hep G2 cells (Wister Institute) were precultured in DMEM (low glucose, 1500 mg/L) containing 10% FCS, penicillin ($1 \times 10^5$ units/L) and streptomycin (100 mg/L), and were cultured at 37° C. in an atmosphere containing 95% air and 5% carbon dioxide. The medium was renewed at an interval of 2 to 3 days. After being confluent, the Hep G2 cells were subcultured as follows: after removing the medium in the dish, the Hep G2 cells were washed quickly with 0.25% trypsin solution (containing 0.1% EDTA), and after addition of a suitable amount of a trypsin solution, incubated at 37° C. for about 5 minutes. Then, a suitable amount of the medium containing 10% FCS was added for termination of the reaction of trypsin, and the Hep G2 cells were suspended well and centrifuged (1000 rpm, 5 minutes) for recovery. The cells were divided into ½–⅓ and were cultured by using a DMEM medium containing 10% FCS. The number of the cells was counted using a Sitemeter. The Hep G2 cells were planted in dishes (3.5 cm) ($85 \times 10^4$ cells/dish) and were cultured by using a DMEM medium containing 1 ml of high glucose (4500 mg/ml) per dish. The Hep G2 cells were made confluent (about $100 \times 10^4$/dish), after which the medium was renewed by the experimental medium, followed by culturing for 24 hours. The Hep G2 cells were washed once with PBS, and after addition of 1 ml of PBS, recovered using a policeman. 0.5 $\mu$ Ci of [$^3$H] glycerol or 0.5 $\mu$ Ci of [$^{14}$C]acetic acid per dish as a radioactive lipid precursor was added before beginning the experiment.

Extraction of Lipid in Hep G2 Cells and the Medium

Lipid in the cells and the medium were extracted according to the method of Bligh and Dyer. The recovered Hep G2 cells were melted and crushed by using a sonicator (Sonifier 250, Bronson Corp.) to give cell homogenate. A part of the cell homogenate was taken into a spitz tube with a screw cap, 3 ml of methanol and 1.5 ml of chloroform were added thereto, followed by stirring well. The mixture was heated at 37° C. for 40 minutes, and 1.5 ml of chloroform and 1.6 ml of water were added thereto to give a mixture wherein the ratio of chloroform : methanol : water was 1:1:0.8, which was then centrifuged (3000 rpm, 15 minutes). The lower-layer chloroform was recovered, concentrated under a nitrogen gas atmosphere and dissolved in a definite amount of petroleum ether, and lipid in the cells was extracted. Lipid in the medium was also extracted in the same manner.

4. Analysis of Lipid

The extracted lipid was fractionated into free cholesterol, cholesterol ester, diglyceride, triglyceride, etc. by using a silica gel G (0.25 mm in thickness)-thin layer chromatography (TLC) developing with petroleum ether : diethyl ether : acetic acid (82:18:1). After completion of the development, each of lipid fractions was detected by coloring with iodide vapor. After the fractionation with TLC, the silica gel of each fraction on the plate was taken into a vial for measurement, dissolved in Sintisol EX-H (Dojin Chemical Co.), and the radioactivity in each fraction was measured with a liquid scintillation counter (Wallac 1410, Pharmacia Co.). Correction was made for the background radioactivity and for quenching by the silica gel.

5. Determination of Cellular Protein

A part of the cell homogenate was used for determination of the protein according to the method of Lowry.

6. Statistical Analysis

Data obtained by the experiment were treated statistically by using Duncan's multiple test.

[Results]

Table 4 shows effect on the excretion of the labeled lipid (cholesterol ester, free cholesterol and triglyceride) after 24 hours by incorporating [$^{14}$C]acetic acid into Hep G2 cell lipid medium. The excretion of the labeled lipid in T+γ group was more significantly inhibited than that in the other groups.

Table 5 shows effect on the excretion of the labeled lipid (total lipid, triglyceride and diglyceride) after 24 hours by incorporating [$^3$H]glycerol into Hep G2 cell lipid medium. The excretion of the labeled lipid in T+γ group was more significantly inhibited than that in the other groups.

TABLE 4

| Labeled lipid | [$^{14}$C] dpm 10$^3$/mg protein |
|---|---|
| Cholesterol ester | |
| C Group | 2.33 |
| T Group | 1.36 |
| T + γ Group | 0.93 |
| Free cholesterol | |
| C Group | 9.65 |
| T Group | 6.43 |
| T + γ Group | 4.60 |
| Triglyceride | |
| C Group | 5.86 |
| T Group | 4.26 |
| T + γ Group | 3.78 |

TABLE 5

| Labeled lipid | [$^3$H] dpm 10$^3$/mg protein |
|---|---|
| Total lipid | |
| C Group | 7.90 |
| T Group | 6.34 |

TABLE 5-continued

| Labeled lipid | [$^3$H] dpm 10$^3$/mg protein |
|---|---|
| T + γ Group | 4.30 |
| Triglyceride | |
| C Group | 2.34 |
| T Group | 1.84 |
| T + γ Group | 1.22 |
| Diglyceride | |
| C Group | 0.17 |
| T Group | 0.05 |
| T + γ Group | 0.05 |

What is claimed is:

1. A pharmaceutical preparation for treating or preventing hyperlipemia comprising taurine and γ-oryzanol as effective components.

2. The pharmaceutical preparation of claim 1 wherein the ratio of taurine to γ-oryzanol is within the range of 300:1 to 10:1.

3. A method for treating or preventing hyperlipemia in a mammal which comprises administering to said mammal a pharmaceutical preparation containing taurine and γ-oryzanol as effective components.

4. The method of claim 3 wherein the ratio of taurine to γ-orzyanol is within the range of 300:1 to 10:1.

* * * * *